(12) United States Patent
Spandorfer

(10) Patent No.: US 11,690,970 B2
(45) Date of Patent: Jul. 4, 2023

(54) AUTOMATED DRUG DISPENSING SYSTEMS WITH AUTOMATED HME BYPASS FOR VENTILATOR CIRCUITS

(71) Applicant: iDTx Systems, Inc., Charleston, SC (US)

(72) Inventor: Michael Spandorfer, Charleston, SC (US)

(73) Assignee: iDTx Systems, Inc., Charleston, SC (US)

( * ) Notice: Subject to any disclaimer, the term of this patent is extended or adjusted under 35 U.S.C. 154(b) by 569 days.

(21) Appl. No.: 16/734,953

(22) Filed: Jan. 6, 2020

(65) Prior Publication Data

US 2020/0147332 A1 May 14, 2020

Related U.S. Application Data

(62) Division of application No. 14/925,553, filed on Oct. 28, 2015, now Pat. No. 10,561,814.

(Continued)

(51) Int. Cl.
*A61M 16/08* (2006.01)
*A61M 16/10* (2006.01)
(Continued)

(52) U.S. Cl.
CPC ...... *A61M 16/0833* (2014.02); *A61M 15/008* (2014.02); *A61M 16/0883* (2014.02);
(Continued)

(58) Field of Classification Search
CPC .. A61M 16/08; A61M 16/0833; A61M 16/10; A61M 16/103; A61M 16/1035;
(Continued)

(56) References Cited

U.S. PATENT DOCUMENTS 4,558,710 A 12/1985 Eichler
4,604,093 A 8/1986 Brown et al.
(Continued)

FOREIGN PATENT DOCUMENTS

GB 2055046 2/1981
WO WO 98/31413 7/1998

OTHER PUBLICATIONS

Ari et al., A Guide to Aerosol Delivery Devices for Respiratory Therapists, 2$^{nd}$ Edition, American Association for Respiratory Care, © 2009, Exemplary pp. 22, 24 and 34.
(Continued)

*Primary Examiner* — LaToya M Louis
(74) *Attorney, Agent, or Firm* — Myers Bigel, P.A.

(57) ABSTRACT

Dispensing systems for a ventilator circuit having a ventilator flow circuit with a normal inhalation flow path with a heat and moisture exchanger (HME), a flow sensor in communication with the ventilator circuit, an automated drug dispensing system with an actuator and a pressurized canister residing upstream of the HME, a bypass inhalation flow path residing downstream of the pressurized canister, and at least one electromechanical valve residing in the inhalation flow path to selectively open the valve which can be normally closed to define a closed bypass path. At least one controller opens the at least one electromechanical valve to open the bypass inhalation flow path and close the normal inhalation flow path through the HME only when the flow sensor indicates air flow is in an inhalation direction. Once the valve is open, the actuator dispenses medication through the bypass inhalation flow path to the patient.

12 Claims, 8 Drawing Sheets

Related U.S. Application Data

(60) Provisional application No. 62/081,927, filed on Nov. 19, 2014.

(51) Int. Cl.
*A61M 16/20* (2006.01)
*A61M 16/14* (2006.01)
*A61M 15/00* (2006.01)
*A61M 16/00* (2006.01)

(52) U.S. Cl.
CPC ........ *A61M 16/1045* (2013.01); *A61M 16/14* (2013.01); *A61M 16/202* (2014.02); *A61M 15/009* (2013.01); *A61M 2016/0015* (2013.01); *A61M 2016/0039* (2013.01); *A61M 2205/505* (2013.01); *A61M 2205/581* (2013.01); *A61M 2205/583* (2013.01); *A61M 2205/8206* (2013.01); *A61M 2230/06* (2013.01); *A61M 2230/10* (2013.01); *A61M 2230/42* (2013.01); *A61M 2230/432* (2013.01); *A61M 2230/437* (2013.01); *A61M 2230/46* (2013.01); *A61M 2230/50* (2013.01)

(58) Field of Classification Search
CPC ............ A61M 16/1045; A61M 16/105; A61M 16/106
See application file for complete search history.

(56) References Cited

U.S. PATENT DOCUMENTS

| | | |
|---|---|---|
| 4,819,629 A | 4/1989 | Jonson |
| 4,934,358 A | 6/1990 | Nilsson et al. |
| 4,984,158 A | 1/1991 | Hillsman |
| 5,002,048 A | 3/1991 | Makiej, Jr. |
| 5,020,527 A | 6/1991 | Dessertine |
| 5,103,814 A | 4/1992 | Maher |
| 5,178,138 A | 1/1993 | Walstrom et al. |
| 5,277,175 A | 1/1994 | Riggs et al. |
| 5,284,133 A | 2/1994 | Burns et al. |
| 5,297,543 A | 3/1994 | Larson et al. |
| 5,363,842 A | 11/1994 | Mishelevich et al. |
| 5,392,768 A | 2/1995 | Johansson et al. |
| 5,394,866 A | 3/1995 | Ritson et al. |
| 5,404,871 A | 4/1995 | Goodman et al. |
| 5,431,154 A | 7/1995 | Seigel et al. |
| 5,437,267 A | 8/1995 | Weinstein et al. |
| 5,438,982 A | 8/1995 | MacIntyre |
| 5,474,058 A | 12/1995 | Lix |
| 5,497,764 A | 3/1996 | Ritson et al. |
| 5,507,277 A | 4/1996 | Rubsamen et al. |
| 5,520,166 A | 5/1996 | Ritson et al. |
| 5,522,378 A | 6/1996 | Ritson et al. |
| 5,522,385 A | 6/1996 | Lloyd et al. |
| 5,542,410 A | 8/1996 | Goodman et al. |
| 5,544,647 A | 8/1996 | Jewett et al. |
| 5,560,353 A | 10/1996 | Willemot et al. |
| 5,564,414 A | 10/1996 | Walker et al. |
| 5,608,647 A | 3/1997 | Rubsamen et al. |
| 5,617,844 A | 4/1997 | King |
| 5,622,162 A | 4/1997 | Johansson et al. |
| 5,622,163 A | 4/1997 | Jewett et al. |
| 5,655,516 A | 8/1997 | Goodman et al. |
| 5,676,129 A | 10/1997 | Rocci, Jr. et al. |
| 5,694,919 A | 12/1997 | Rubsamen et al. |
| 5,724,957 A | 3/1998 | Rubsamen et al. |
| 5,738,087 A | 4/1998 | King |
| 5,743,252 A | 4/1998 | Rubsamen et al. |
| 5,755,218 A | 5/1998 | Johansson et al. |
| 5,770,585 A | 6/1998 | Kaufman et al. |
| 5,794,612 A | 8/1998 | Wachter et al. |
| 5,809,997 A | 9/1998 | Wolf |
| 5,826,570 A | 10/1998 | Goodman et al. |
| 5,881,716 A | 3/1999 | Wirch et al. |
| 5,967,141 A | 10/1999 | Heinonen |
| 6,012,450 A | 1/2000 | Rubsamen |
| 6,014,972 A | 1/2000 | Sladek |
| 6,079,413 A | 6/2000 | Baran |
| 6,116,234 A | 9/2000 | Genova et al. |
| 6,119,684 A | 9/2000 | Nöhl et al. |
| 6,123,068 A | 9/2000 | Lloyd et al. |
| 6,138,669 A | 10/2000 | Rocci, Jr. et al. |
| 6,148,815 A | 11/2000 | Wolf |
| 6,202,642 B1 | 3/2001 | McKinnon et al. |
| 6,223,744 B1 | 5/2001 | Garon |
| 6,237,597 B1 | 5/2001 | Kovac |
| 6,260,549 B1 | 7/2001 | Sosiak |
| 6,318,361 B1 | 11/2001 | Sosiak |
| 6,325,062 B1 | 12/2001 | Sosiak |
| 6,349,724 B1 | 2/2002 | Burton et al. |
| 6,358,058 B1 | 3/2002 | Strupat et al. |
| 6,390,088 B1 | 5/2002 | Nöhl et al. |
| 6,435,175 B1 | 8/2002 | Stenzler |
| 6,523,536 B2 | 2/2003 | Fugelsang et al. |
| 6,529,446 B1 | 3/2003 | de la Huerga |
| 6,550,476 B1 | 4/2003 | Ryder |
| 6,557,552 B1 | 5/2003 | Cox et al. |
| 6,588,421 B1 | 7/2003 | Diehl et al. |
| 6,595,389 B2 | 7/2003 | Fuchs |
| 6,598,602 B1 | 7/2003 | Sjoholm |
| 6,615,825 B2 | 9/2003 | Stenzler |
| 6,631,716 B1 | 10/2003 | Robinson et al. |
| 6,651,844 B2 | 11/2003 | Tomaka et al. |
| 6,681,767 B1 | 1/2004 | Patton et al. |
| 6,684,880 B2 | 2/2004 | Trueba |
| 6,705,316 B2 | 3/2004 | Blythe et al. |
| 6,725,859 B1 | 4/2004 | Rothenberg et al. |
| 6,830,046 B2 | 12/2004 | Blakley et al. |
| 6,871,645 B2 | 3/2005 | Wartman et al. |
| 6,951,216 B2 | 10/2005 | Heinonen |
| 6,962,152 B1 | 11/2005 | Sladek |
| 7,185,648 B1 | 3/2007 | Rand |
| 7,191,777 B2 | 3/2007 | Band et al. |
| 7,198,044 B2 | 4/2007 | Trueba |
| 7,201,166 B2 | 4/2007 | Blaise et al. |
| 7,201,167 B2 | 4/2007 | Fink et al. |
| 7,347,200 B2 | 3/2008 | Jones et al. |
| 7,347,203 B2 | 3/2008 | Marler et al. |
| 7,495,546 B2 | 2/2009 | Lintell |
| 7,549,421 B2 | 6/2009 | Levi et al. |
| 7,600,511 B2 | 10/2009 | Power et al. |
| 7,634,995 B2 | 12/2009 | Grychowski et al. |
| 7,748,382 B2 | 7/2010 | Denyer et al. |
| 7,905,230 B2 | 3/2011 | Schuler et al. |
| 7,921,846 B1 | 4/2011 | Marler et al. |
| 8,151,794 B2 | 4/2012 | Meyer et al. |
| 8,857,429 B2 | 10/2014 | Spandorfer |
| 8,869,793 B1 | 10/2014 | Spandorfer et al. |
| 9,737,679 B2 | 8/2017 | Ritter, III et al. |
| 2002/0069869 A1 | 6/2002 | Farmer |
| 2002/0069870 A1 | 6/2002 | Farmer |
| 2003/0200964 A1 | 10/2003 | Blakley et al. |
| 2004/0069301 A1 | 4/2004 | Bacon |
| 2004/0084050 A1 | 5/2004 | Baran |
| 2004/0107961 A1 | 6/2004 | Trueba |
| 2004/0138577 A1 | 7/2004 | Kline |
| 2004/0231667 A1 | 11/2004 | Horton et al. |
| 2004/0255936 A1 | 12/2004 | Urbanus |
| 2005/0016528 A1 | 1/2005 | Aslin et al. |
| 2005/0039746 A1 | 2/2005 | Grychowski et al. |
| 2005/0139211 A1 | 6/2005 | Alson et al. |
| 2005/0183725 A1 | 8/2005 | Gumaste et al. |
| 2005/0235987 A1 | 10/2005 | Smaldone et al. |
| 2005/0268908 A1 | 12/2005 | Bonney et al. |
| 2005/0274378 A1 | 12/2005 | Bonney et al. |
| 2006/0021614 A1 | 2/2006 | Wermeling et al. |
| 2006/0254581 A1 | 11/2006 | Genova et al. |
| 2007/0151560 A1 | 7/2007 | Price et al. |
| 2007/0173731 A1 | 7/2007 | Meka et al. |
| 2008/0009761 A1 | 1/2008 | Acker et al. |
| 2008/0308101 A1 | 12/2008 | Spandorfer |
| 2009/0120431 A1 | 5/2009 | Borgschulte et al. |
| 2009/0137920 A1 | 5/2009 | Colman et al. |

(56) References Cited

U.S. PATENT DOCUMENTS

| 2012/0055472 A1 | 3/2012 | Brunnberg et al. |
| 2012/0234321 A1 | 9/2012 | Power et al. |
| 2013/0008436 A1 | 1/2013 | Von Hollen et al. |
| 2014/0251330 A1 | 9/2014 | Collins et al. |

OTHER PUBLICATIONS

Carrillo et al., The Development of an Automatic Metered Dose Inhaler, Vanderbilt University Department of BioMedical Engineering, 32 pages, Apr. 27, 2004.
Carrillo et al., Automated Metered Dose Inhaler Presentation #5, Vanderbilt University Department of Engineering, 11 pages, dated Apr. 7, 2004.
CircuVent® Ventilator Support Products, www.smiths-medical.com, printed from the internet Nov. 18, 2014, 9 pages.
European Office Action Corresponding to European Patent Application No. 08770987.9; dated Feb. 28, 2014; 10 Pages.
European Patent Office communication of a Decision to Grant a European Patent pursuant to Article 97(1) EPC corresponding to European Patent Application No. 08770987.9, 2 pp. (dated Nov. 17, 2016).
International Search Report and Written Opinion for corresponding PCT Application No. PCT/US2008/066883, dated Oct. 1, 2008.
OHMEDA Project: Automated Metered-Dose Inhaler Deliver Device, Biomedical Engineering Design Projects, College of Engineering University of Wisconsin-Madison, printed from http://homepages.cae.wisc.edu/, printed Jul. 3, 2008, 4 pages, final poster presentation and demo stated to be date May 10, 2002.
Product Specification and Directions, Metered Dose Inhaler (MDI) Adapter, Instrumentation Industries, Inc., 2 pages, (Date of first publication unknown but for exam purposes only, is to be considered before the priority date of the instant application.)

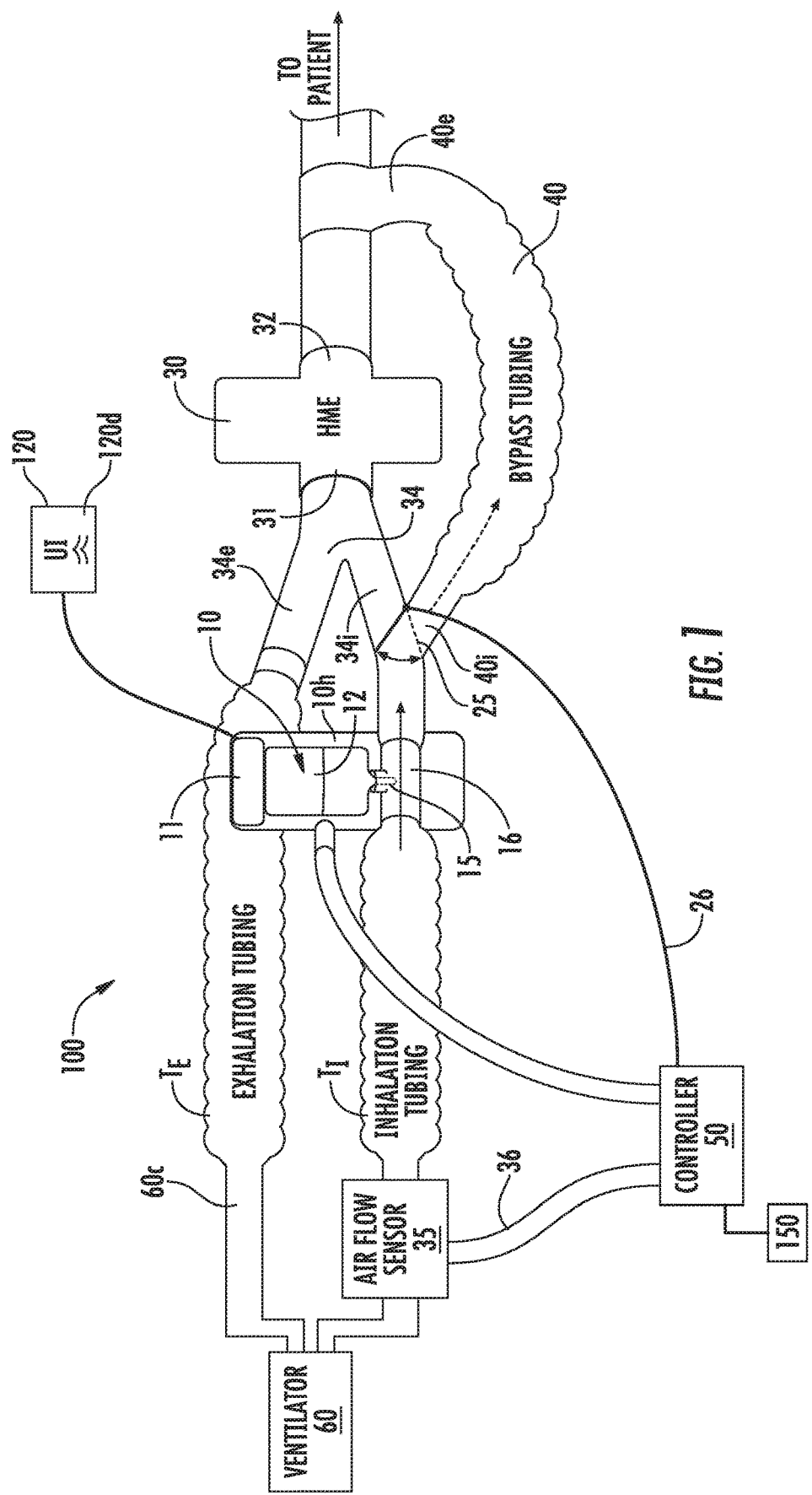

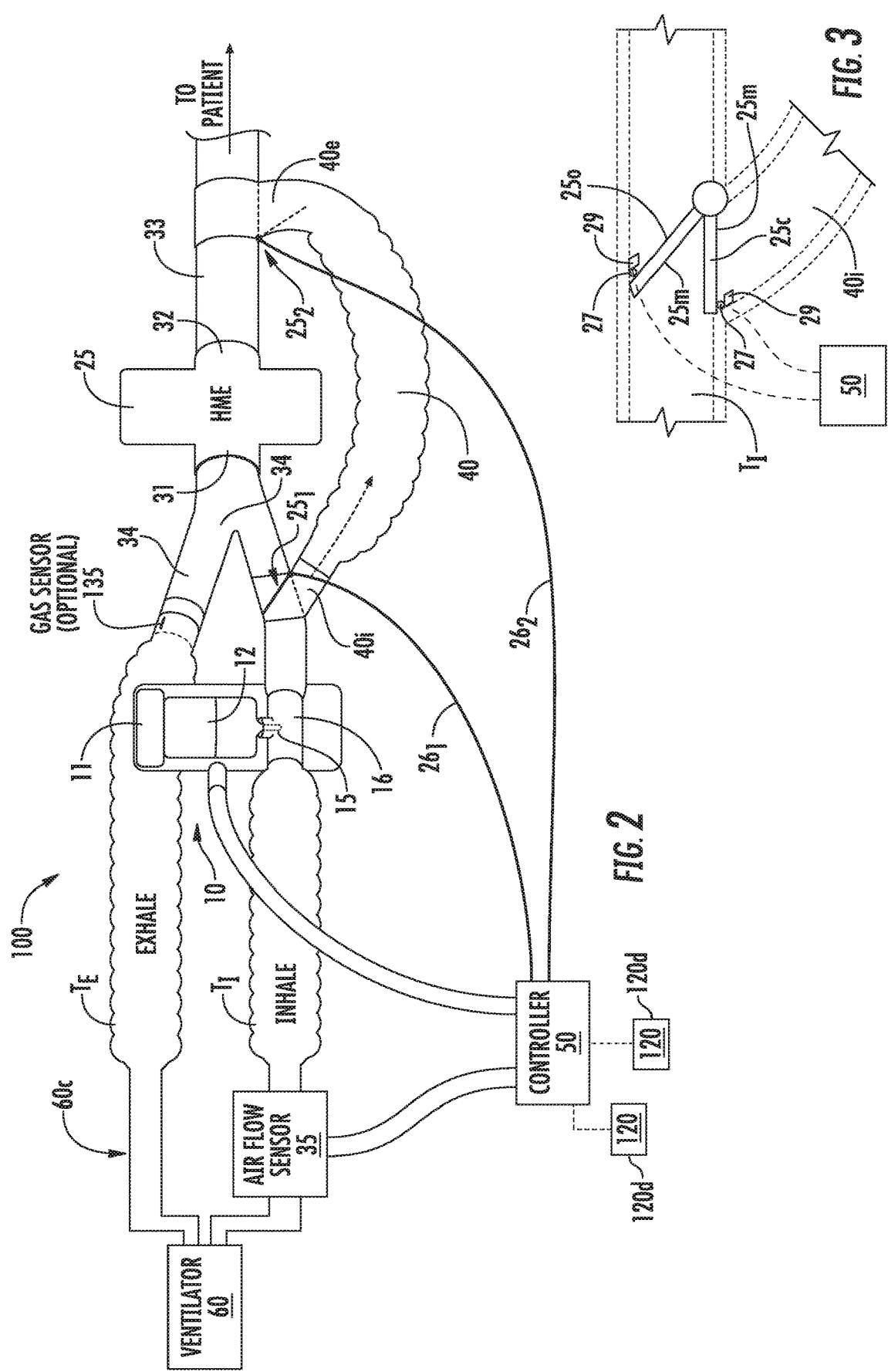

AUTOMATED DRUG DISPENSING SYSTEMS WITH AUTOMATED HME BYPASS FOR VENTILATOR CIRCUITS

RELATED APPLICATIONS

This application is a divisional application of U.S. patent application Ser. No. 14/925,553, filed Oct. 28, 2015, which claims the benefit of and priority to U.S. Provisional Application Ser. No. 62/081,927 filed Nov. 19, 2014, the contents of which are hereby incorporated by reference as if recited in full herein.

FIELD OF THE INVENTION

This invention relates to ventilators and to drug dispensing systems.

BACKGROUND

Mechanical ventilation is a method of mechanically assisting or replacing spontaneous breathing when patients cannot do so. One type of ventilation system employs the use of an endotracheal or tracheostomy tube secured into a patient's upper respiratory tract. Gas is mechanically delivered to the patient via the tube. In many cases, mechanical ventilation is used in acute settings such as an intensive care unit for a short period of time during a serious illness. Currently, the main form of mechanical ventilation is positive pressure ventilation, which works by increasing the pressure in the patient's airway and thus forcing additional air into the lungs. To aid in the treatment of ventilated patients, aerosol medicines are aspirated in situ through an access point in the ventilator system. Conventionally, this process is manual, requiring the medical professional to deliver the aerosols on a regular basis.

Automatically administering medication to mechanically ventilated patients may reduce healthcare costs and improve patient safety.

SUMMARY

Embodiments of the present invention relate generally to systems for respiratory therapy, particularly to ventilator systems that include heat and moisture exchanger (HME) media or heat and moisture exchanger (HME) media in the respiratory path and also provides the additional capability of automated dispensing of aerosol medication to a patient effectively without interrupting the respiratory path.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 1 is a schematic illustration of an automated drug dispensing system suitable for use with ventilator circuits having an HME according to some embodiments.

FIG. 2 is a schematic illustration of an alternate automated dispensing system according to some embodiments.

FIG. 3 is a schematic illustration of an automated open and closed valve arrangement for a bypass flow path according to some embodiments.

DETAILED DESCRIPTION OF EMBODIMENTS OF THE INVENTION

Figure 4:
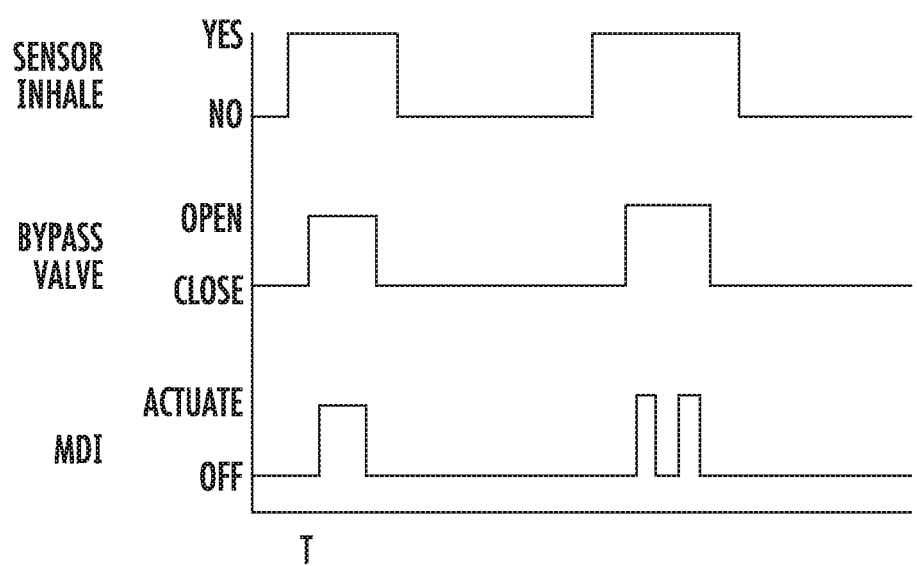
FIGS. 4 and 5 are schematics exemplary timing diagrams according to some embodiments.

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout.

Thicknesses and dimensions of some components may be exaggerated for clarity. Broken lines illustrate elements or features not visible from the presented view (e.g., on the opposite side) or as an optional element unless otherwise indicated. It will be understood that when an element is referred to as being "attached," "connected," or "coupled" to another element, it can be directly connected or coupled to the other element or intervening elements may be present. In contrast, when an element is referred to as being "directly attached," "directly connected," or "directly coupled" to another element, there are no intervening elements present. Also, although a feature is described with respect to one embodiment, this feature may be used with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about" when used with a numerical values means that the numerical value can vary by +/−20%.

Turning now to the figures, a ventilator system 100 with an automated drug dispensing control and delivery system 10 is illustrated in FIG. 1. The automated drug dispensing system 10 can be used to provide controlled and automated delivery of an inhalable substance (e.g., medication) to a ventilator circuit 60c of a ventilator 60 of the ventilator system 100.

In some embodiments, the dispensing system 10 can include a housing 10h that can hold the actuator 11. The housing 10h can be a compact, light-weight device that can reside directly on tubing in the ventilator tubing system, typically in fluid communication with the inhalation tubing upstream of the heat and moisture exchanger (HME) 30.

The HME 30 is typically passive without requiring active heating or humidification as is known to those of skill in the art. However, active HMEs may also be used. A commercially available HME, which uses a bypass flow path, is the CIRCUVENT® sold by Smiths Medical.

As illustrated in FIG. 1, the system 10 can be configured to have a housing 10h that releasably attaches pressurized canister 12, such as a metered dose inhaler (MDI) canister. The pressurized canister 12 can comprise, for example, a pressurized MDI (pMDI) or Dry Powder Inhaler (DPI) canister. The canister 12 may be snugly and releasably held by the housing 10h or by components within the housing 10h. The dispensing system 10 has at least one actuator 11 which is in communication (hard wired or wireless) with at least one controller 50 to automatically depress the nozzle 15 of the canister 12 to dispense medication at a desired delivery time which may be set according to a dispensing schedule and/or may be manually dispensed by a clinician or other authorized user. For further discussions of exemplary automated drug dispensing systems, see, e.g., U.S. Pat. Nos. 8,869,793 and 8,857,429, the contents of which are hereby incorporated by reference as if recited in full herein. The dispensing system 10 can include a bi-directional, compact tubular MDI spacer 16 that can reside directly under the nozzle 15 (with the nozzle residing enclosed by the spacer 16). The actuator 11 can reside above an upper end of the canister 12 and can automatically actuate to release medication therefrom, synched to only release toward the patient (inhalation) airflow direction.

As shown in FIG. 1, the HME 30 has a ventilator facing side 31 and a patient facing side 32. The patient facing side 32 faces the endotracheal tube that resides in a patient "P". The patient facing side 32 of the HME 30 can be connected to an endotracheal tube (not shown) in the patient. The ventilator side of the HME 30 can be connected to a Y connector 34. One leg or fork 34i of the "Y" connector 34 can connect to the inhalation tubing $T_I$ and the other leg or fork 34e can connect to the exhalation tubing $T_E$.

The inhalation connector leg or fork 34i of the Y connector 34 can be connected to one end of a (typically flexible) bypass tube 40 having its other end of the bypass tube 40 connected to tubing 33 downstream of the HME 30, closer to the endotracheal tube inside the patient P. The inhalation connector leg or fork 34i can include at least one internal electromechanical flow valve 25 that is configured with a valve member 25m that is normally closed to close the intake region 40i of the bypass tubing from the inhalation flow path.

As shown in FIG. 3, the at least one valve 25 can be opened to an open configuration 25o that is automatically opened when aerosol is injected or dispensed to the inhalation flow path by the dispensing system 10 to close the "normal" inhalation flow path through the HME to totally bypass the HME to avoid medication delivered by the dispensing system 10 being trapped in the media of the HME or any filter material of the HME. The controller 50 can then automatically close the valve 25 to have a closed configuration 25c to close the intake of the bypass tubing 40i to direct inhalation flow through the HME 30 and the normal inhalation flow path.

The at least one flow valve 25 can be located at various locations along the inhalation flow path, including upstream, instead of downstream, of the actuator 12. The bypass flow valve 25 can reside upstream of the Y connector 34 (where used).

In some embodiments, the ventilator circuit 60c can include three or more inhalation flow path tubes (FIGS. 8A/8B) to provide the normal and the bypass inhalation flow paths, with the bypass flow path potentially being as long as the normal inhalation flow path, to deliver the dispensed medication. Also, the at least one flow valve 25 can reside in a tube or tube connector that can be above or below the actuator 11 for the canister 12.

Various types of medical grade valves can be used for the at least one valve 25. As shown in FIG. 3, the valve 25 can be configured with a pivoting internal member 25m that pivots to open and close the two different flow paths (the normal and bypass flow paths). The pivoting internal member 25m may be flat.

As also shown in FIG. 3, the internal wall of the normal and bypass inhalation flow paths at the valve 25 can have internal members 27 that cooperate with the outer end of the valve member 25m to close the normal flow path and the bypass flow path at the two valve positions. The internal members 27 can comprise a ledge, O-ring, gasket, resilient plug or other feature or combination of features to act as a stop and/or seal. The internal members 27 may also include a sensor 29 that electronically, positively confirms that the valve 25 is open with the valve member 25m in the appropriate location, closed against the normal flow path, during dispensing of the medication. The valve 25 can also or alternatively include a gasket, O-ring or other sealant. The sensor 29 may be in communication with the at least one controller 50. The at least one controller 50 can generate an alarm if the valve is malfunctioning, e.g., not opening before, during or slightly after the medication is dispensed.

Other types of medical grade valves can be used for the at least one valve 25. For example, a ball valve can be used, which may provide for rapid shut-off, since a 90° turn offers complete a shut-off angle.

In some embodiments, first and second valves upstream of the HME 30 may be used, one to shut the normal flow path through the HME 30 and the other to open the bypass path 40. The first and second valves may comprise butterfly valves or other valve configurations. The first and second valves can be operated with a defined sequence, e.g., open bypass concurrently with the closing of the normal flow path through the HME or open the bypass path, then rapidly close the normal bypass flow path within 0.1 seconds to 2 seconds, for example.

In some embodiments, the at least one valve 25 may be configured as a disc valve, a diaphragm valve, a gate valve, a knife valve, and/or a plug valve, by way of example.

In some embodiments a check valve (e.g., a one way valve) may be positioned at the egress end of the inhalation bypass tube 40e to inhibit exhalation flow in the bypass tube 40 thereby reducing "dead volume."

The at least one valve 25 includes an electrical connection 26 (wired or wireless) to at least one controller 50 for automated operation in synchronization with inhalation air flow based on input from an air flow sensor 35 and/or the ventilator 60. The actuator 11 can also include an electrical (wired or wireless) connection to the at least one controller 50. The sensor 35 can include at least one electrical (wired or wireless) connection 36 to the at least one controller 50.

While the at least one valve 25 is shown using a "Y" connector upstream of the HME 30, other flow circuit 60c configurations may be used.

The at least one controller 50 can be a single controller or may be a plurality of controllers which may be in a common location or distributed. The at least one controller 50 can monitor inhalation air flow direction using data from an air flow sensor 25 and/or ventilator 60, direct the actuation of the actuator 11 to only actuate when air flow is in the inhalation direction and open the normally closed valve 25 to open the bypass valve when the actuator is actively dispensing or within a defined time before and/or after a dispensing. The dispensing system 10 may be configured to provide different numbers of actuations per inhalation for custom dosing. FIG. 4 illustrates an exemplary timing diagram for the cooperating components. When the controller 50 detects data from the sensor that indicates air flow is in the inhalation direction (sensor inhaler Y), the bypass valve is opened and the MDI actuator is actuated one or more times. The bypass valve 25 is automatically closed to return the inhalation path to "normal" through the HME after the dispensing by the dispensing system 10 is complete which may be before a single inhalation cycle is complete, as shown.

The at least one valve can be a single valve 25 or may comprise a plurality of valves. For example, the at least one valve 25 can include a first valve $25_1$ at the intake to the bypass tubing 40i and a second valve $25_2$ at the egress of the bypass tubing 40e as shown in FIG. 2. The controller 50 can be used to control the operation of both valves $25_1$, $25_2$ as shown in FIG. 5, for example.

Figure 5:
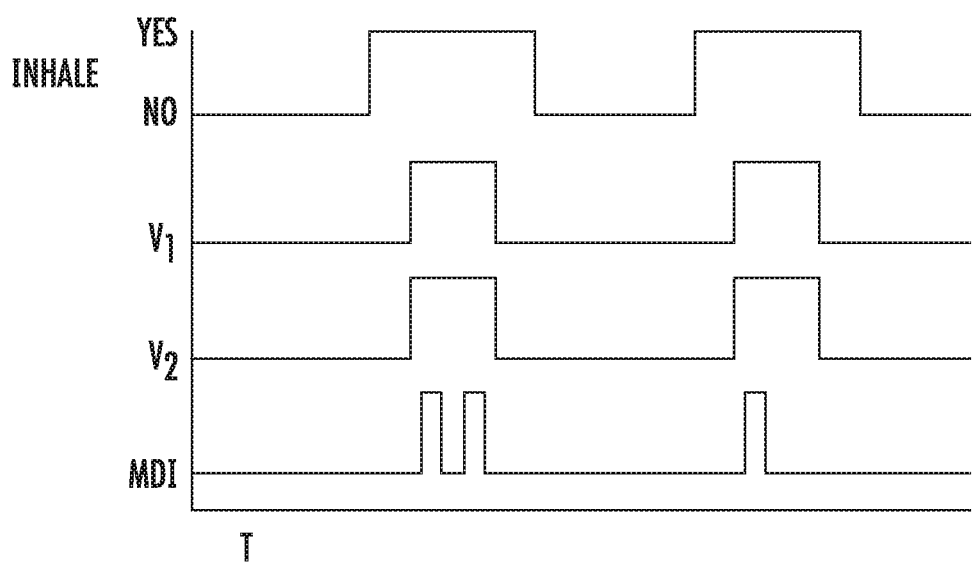

With respect to FIGS. 4 and 5, the at least one controller 50 can be configured to open the valve(s) 25 only when air flow is toward the patient, close the valve after the medication delivery, e.g., within about 5-30 seconds of a puff or successive puffs, where a dose uses same as the dosing is predefined, the controller knows when a medication dose has been completed and the valve(s) 25 can be closed shortly thereafter (e.g., within 1-10 seconds) of a completed dose, depending on flow rate of a patient so that all medicine is delivered through the bypass tube 40 or at least into the bypass tube 40i (where one valve is used and it is placed at the intake, for example). The dispensing can be terminated if air flow is reversed even if a dose is not complete and the dosing can then be carried out in a subsequent inhalation flow cycle.

The at least one valve 25 can be configured to automatically return to the closed state a defined time after it is open without being directed to close by the at least one controller 50. For example, the at least one valve 25 can be biased to return to the closed configuration after it is open or may have a timer that directs the closure independent of the controller 50. However, typically the at least one controller 50 can direct the at least one valve 25 to return to a defined home state.

Figure 8A:
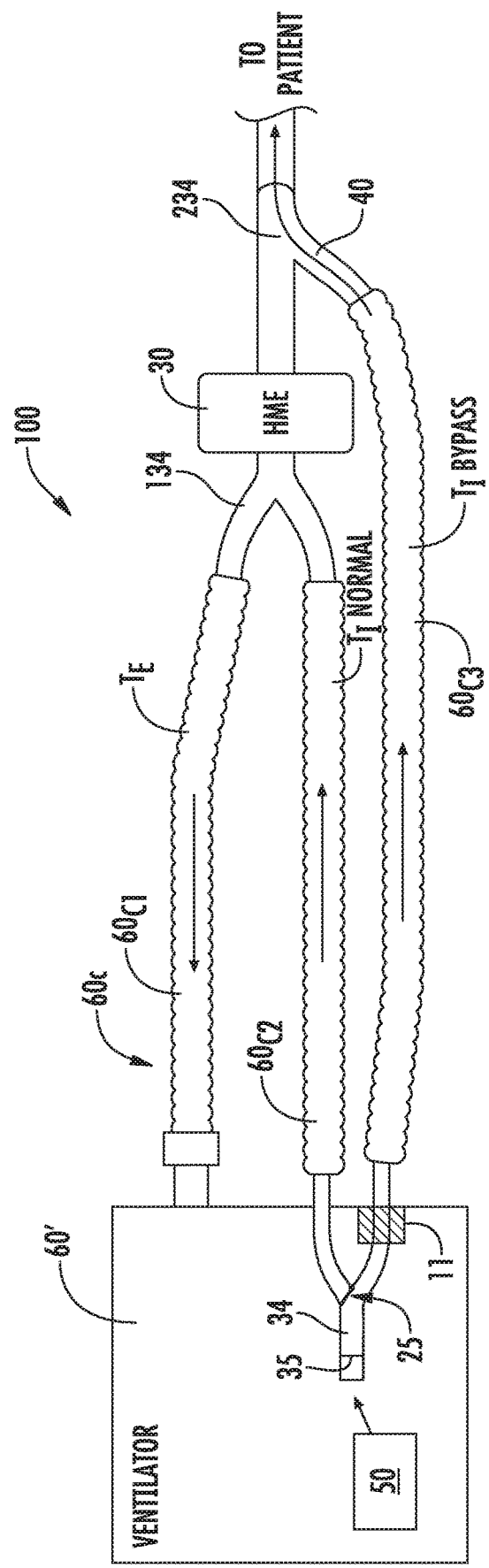
FIGS. 8A and 8B are schematic illustrations of a hybrid ventilator with an onboard bypass control (and optional onboard drug dispensing control) for a flow valve that allows two different inhalation flow paths so a bypass flow path can be automatically used to avoid an HME when a drug is being dispensed according to embodiments of the present invention.
Figure 8B:
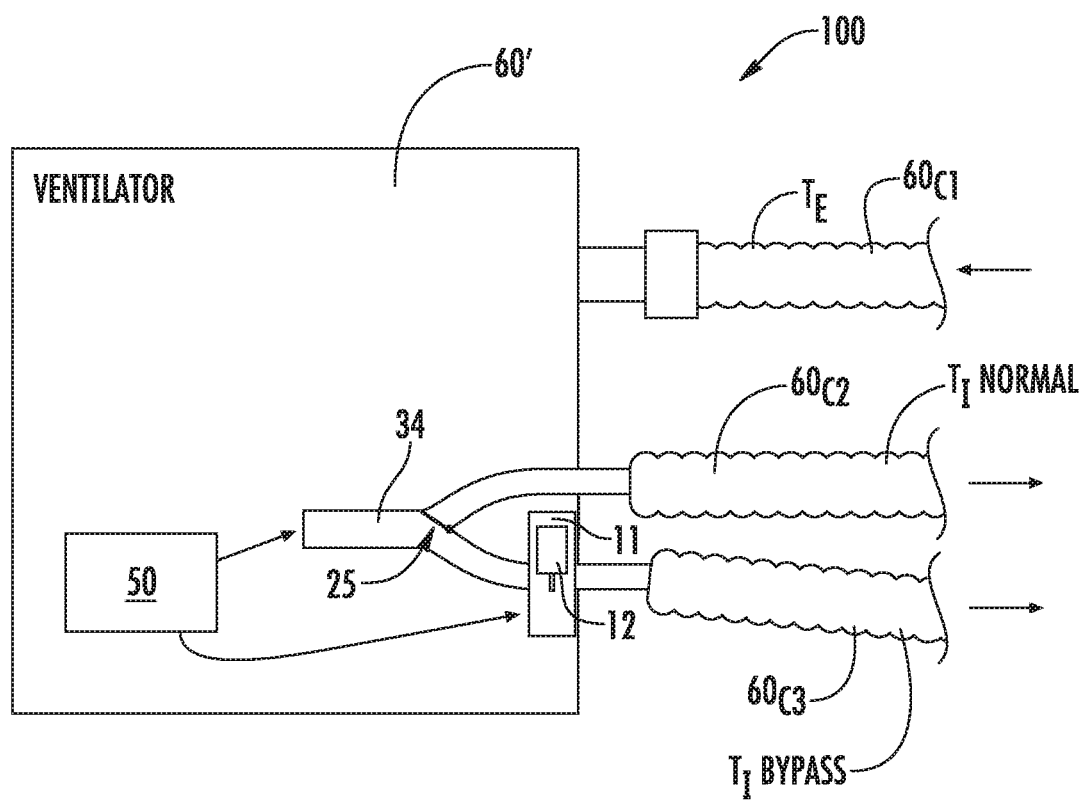

As shown in FIGS. 8A and 8B, the dispensing system 10 and bypass flow valve 25 for the inhalation flow path $60c_3$ that delivers the dispensed medication can be onboard and/or held in a housing of a ventilator unit 60'. The ventilator circuit 60c can be configured to have three defined circuit segments $60c_1$, $60c_2$, $60c_3$, including a bypass inhalation flow path $60c_3$ for delivering the medication when the valve 25 is open and a normal inhalation flow path through the HME 30 when the valve 25 is closed. The ventilator controller 50 can include a processor 160 can be configured to control the actuation of the actuator 11 and the valve 25. The ventilator circuit 60c can include at least three "Y" connectors 34, 134, 234, with one Y connector in or held by the ventilator housing as shown.

The direction of air flow (exhale/inhale) may optionally be determined by a sensor 35, which can be placed at a number of locations along the ventilation flow circuit 60c and/or by the operation of the ventilator 60, 60' itself.

As shown in FIGS. 8A and 8B, the one or more actuators 11 for one or more canisters 12 can also be onboard the ventilator unit 60' and in communication with the onboard controller 50.

The embodiments shown in FIGS. 8A and 8B can be described as a hybrid ventilator 60' with a controller 50 (e.g., at least one microprocessor) that can be onboard or integrated into the ventilator unit to allow the ventilator 60' to have an automated bypass control for the at least one flow valve 25 that may reside inside the ventilator unit or in one or both of the alternate inhalation flow paths. The hybrid ventilator 60' can also include an optional onboard drug dispensing control for the actuator 11 of the canister 12 that allows automated flow path selection synchronized to an appropriate bypass flow path that avoids the HME 30 when a drug is being dispensed according to embodiments of the present invention The dispensing system 10 can be configured to be dynamic, responsive to the patients physiologic parameters. That is, the dispensing system 10 (whether a separate system or incorporated into the ventilator 60) can be a "smart" device that will actuate automatically in accordance to a preset algorithm based-off the patient's current (bedside) physiologic status including but not limited to, one or more of the following parameters which can be electronically periodically or continuously monitored by the system 10 and/or 60' or by devices in communication therewith: heart rate, respiratory rate, airway resistance, blood pressure, minute ventilation, end tidal carbon dioxide measurements, temperature, EEG monitoring, cardiac telemetry rhythm/ECG monitoring, oxygen saturation/oximetry monitoring peripheral or central, nitric oxide exhaled. The term "minute ventilation" is well known and refers to a measured parameter of the ventilator, e.g., Resp rate×tidal volume.

As illustrated in FIG. 1, the dispensing system 10 (whether separate or onboard the ventilator 60') can include an operator user interface 120 with a display 120d which may be onboard the housing 10h and/or a separate device. An operator can control the number of doses to be supplied from the canister 11 via the UI. The operator can also control the frequency of the supplied doses via the UI. Thus, these controls allow the dispensing system 10 to be programmed to selectively provide a desired, adjustable and automated delivery of medication to a respective patient from the MDI 11 to the connector ventilator flow circuit 60c. It is noted that the UI can be various input devices such as GUIs, electronic pull-down menus, buttons, wheels, or the like. Moreover, the operator interface 120 can be integrated with one or more displays, which can be a GUI touch screen display onboard the housing 10h and/or on smartphones, electronic notebooks, electronic notepads and other pervasive computing devices. The UI may include icons or other features providing the user input, for example.

The display 120 can configured to display certain information and operational parameters. For example, the doses remaining (i.e., the number of doses input by the operator or the number of doses associated with the MDI 11 less the number of doses already administered) may be displayed. The number of doses need not necessarily match the number of actuations as a patient may need more than one "puff per dose." In some embodiments, the system 10 can be configured to track and/or display the number of actuations or "puffs." MDIs are sometimes prepackaged and pre-measured with a defined number of actuations or puffs (e.g., 60 to 400 actuations or puffs). Because the number of puffs per dose may vary based on a patient and/or a physician's orders, the unit can track the actuations or puffs to provide information and audible, visual or other warning as to when the MDI canister 11 will be empty or should be replaced. It is noted that although the system 10 can track or measure actuations (puffs), the dispensing system 10 can also be programmed such that this information is converted to doses for a particular patient.

The interval between doses may also be displayed on the display 120d. Other information such as the "status" of the MDI 11 can also be displayed. For example, the status may read "on" when the MDI is operating under an automated mode with defined programmed parameters or "off" if the MDI is not in an automated mode. The status may also inform the operator whether the MDI has been installed correctly and/or whether the MDI is operational in general. The controller 50 (FIGS. 1, 2) can continuously or at various times dynamically update the various information and parameters on the display 120 based on user input and/or based on the operation of the system 10.

In some embodiments, all operational information can be displayed on the display 120d together. Alternatively, the information may scroll along the display 120d and/or the display 120d may toggle between different screens containing different information. The display UI control may allow the operator to manually perform these scrolling and toggling operations. The display UI control may also power the display "on" and "off" in some embodiments. The display 120d may power "on" and "off" at various intervals for a power-saving mode. An "on" display mode may be triggered by a proximity sensor or by a clinician's manual input or at selected or pre-set time intervals. The display 120d may automatically operate prior to actuation and just after then go into power-saving mode.

Power may be provided to the system 10 via a medical grade AC or DC power supply 150. The dispensing system 10 may include a battery to allow the unit 10 to function if the AC or DC power supply is interrupted. Alternatively, the power may be provided by an on-board housing battery and the system 10 can include one or more backup batteries. It is contemplated that various components could be powered by different power sources. For example, the actuator 11, display 120d, controller 50 and valve 25 may be powered by different power sources.

In operation, the controller 50 can direct an agitator to agitate the canister 12 just prior to actuation and delivery of the medication based on the selected delivery frequency. The controller 50 can direct the actuator 11 to actuate the canister 12 to dispense medication into the inhalation flow path $T_I$ of the ventilator flow circuit 60c. The controller 50 times the actuation such that the medication is dispensed while the flow of gas through the tubular (spacer) connector 16 is toward the patient (i.e., while the patient inhales) and the at least one bypass valve 25 is open to force the medication to travel through the bypass valve to the patient to avoid the HME. This flow direction is indicated by the arrows to the right in FIG. 1.

It is noted that two or more successive actuations could equal one dose where the dose is two or more "puffs" and the dose counter can indicate the number of doses remaining (shown by schematic example in FIG. 4 as two successive "puffs" during one inhalation cycle). As described above, the number of puffs can also be displayed and/or monitored. Because the rate at which puffs will be delivered may be programmed, the system 10 can further calculate, monitor and/or display the time at which the MDI canister 12 will be empty or lacking sufficient puffs for a desired dose. For example, the display 120d could show the number of puffs remaining, and how many hours and minutes remain before the canister is empty (or the date and/or time at which the canister will be empty).

The gas flow sensor 35 can be disposed in the connector 16 (or elsewhere in the ventilator circuit 60c) to detect incoming air from the ventilator V and exhaled breath from the patient P. In other words, the gas flow sensor 35 can measure or sense the direction of the flow of gas through the tubing $T_I$, and/or connector 16 (or the ventilator circuit 60c) and communicate the same to the controller. As described above, the release of medication from the canister 12 can be timed so that the medication flows with the gas toward the patient. The gas flow sensor 35 or a different sensor may further verify that the medication properly reaches the patient and may communicate the same to the controller 50.

The gas flow sensor 35, or an additional sensor, may be used to measure pressure and/or the rate of change of pressure in the ventilator flow circuit, and may measure other gas flow characteristics such as volumetric gas flow rate and temperature, that indicate the patient's ability to receive the medication. The gas flow sensor 35 can measure ventilator flow circuit conditions and patient airway resistance, which may be used to determine the need for additional medication dosing and timing or modulation of the current specified dosing and timing of the medication. Higher pressure and/or a relatively short cycle time on reversal of gas flow may indicate that the ability of the patient to consume the medication through the lungs is impaired. In such case, the controller 50 may increase the dosage frequency or dosage amount to the patient or both. The adjustment may occur manually or automatically by an algorithm utilized by the controller 50. Similarly, to wean the patient, the frequency and/or dose amount can be reduced when patient airway resistance improves.

The sensor(s) described herein and other sensors may perform other functions as described in U.S. Pat. Nos. 8,857,429 and 8,869,793, the disclosures of which are incorporated by reference as if disclosed herein in its entirety.

The dispensing system 10 can include a manual override UI control 32. The operator may use this control to deliver an unscheduled release of medication, such as if the respiratory condition of the patient appears poor or upon an order from the doctor. The counter on the display (e.g., "doses or puffs remaining") will generally be decremented following use of the manual override.

The dispensing system 10 may include other features. For example, the dispensing system 10 may have a shutoff control to immediately cease the automated functions (for example, in an emergency situation). The shutoff control may be part of the operator interface panel 120 or may be a separate switch on the housing 10h.

The dispensing system 10 may also provide alarms for various events, such as when the unit 10 is malfunctioning (e.g., one or more components have stopped operating) or when the MDI canister 12 is depleted of medication or approaching this state. The alarms may be visible alarms on the display 120d and/or audible alarms. The alarms may be sent to one or more of a PDA, cell phone, notepad, or other device carried by a clinician such as a nurse and/or a monitoring station.

The dispensing system 10 may include certain features to enhance security and patient safety. For example, the operator may need to enter a password prior to operating the dispensing system 10. The password may be entered via UI controls on the operator interface panel 120, for example. The dispensing system 10 may also include or communicate with one or more identification devices and can include one or more optical or electronic devices. For example, the operator may be required to enter (e.g., swipe) or scan a badge or authorized key fob or other identification prior to operating the unit. The housing or other part of the dispensing system 10 can include an on-board reader that recognizes authorized users via biometrics, magnetic data strips, digital information memories and the like.

The dispensing system 10 can be configured for pre-defined product data for a particular patient. Thus, the MDI canister 12 may be electronically identified (e.g., via a bar code label) by the dispensing system 10 before or during installation in the housing 10 or before operation of the system 10 to help ensure the proper medication is being administered. For example, the system 10 can include an optical reader that electronically reads a label on the MDI canister (the MDI canister may need to be rotated to have the correct orientation before allowing automated dispensing). Other identification devices, such as RFID tags, may be implemented instead of bar codes. The system 10 may also store information about each MDI drug and about the patient so it can alert the operator to drug incompatibilities or to prevent programming an overdose and generally reduce drug administration errors.

Furthermore, the patient may be identified in a variety of ways prior to administering medication. For example, the system 10 can be programmatically locked, and the operator must identify the proper patient identification to unlock the unit housing 10h (e.g., after loading the canister 12). That is, the dispensing system 10 may be configured to have a patient-specific code that an operator must use to operate or change the MDIs in the housing 10h.

Other methods of automating and controlling the system 10 are contemplated. For example, the system 10 may include and/or communicate with a wireless handheld device (such as a PDA, cell phone, notepad or smartphone). The handheld device may be used along with, form the interface panel or be used with another user interface panel to input parameters such as the number and frequency of doses.

The dispensing system 10 can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

The dispensing systems 10 may include a web portal that controls participant access. The web portal may be configured to be user-specific based on defined privacy or privilege levels of the user. That is, each web client can display a different web portal configuration and/or different web pages associated with a specific user type (showing different permissible actions, commands and data options). Where used, a server can provide a centralized administration and management application. The server can include or communicate with a plurality of databases including participant/user profiles, a security directory, routing security rules, and patient records.

Figure 6:
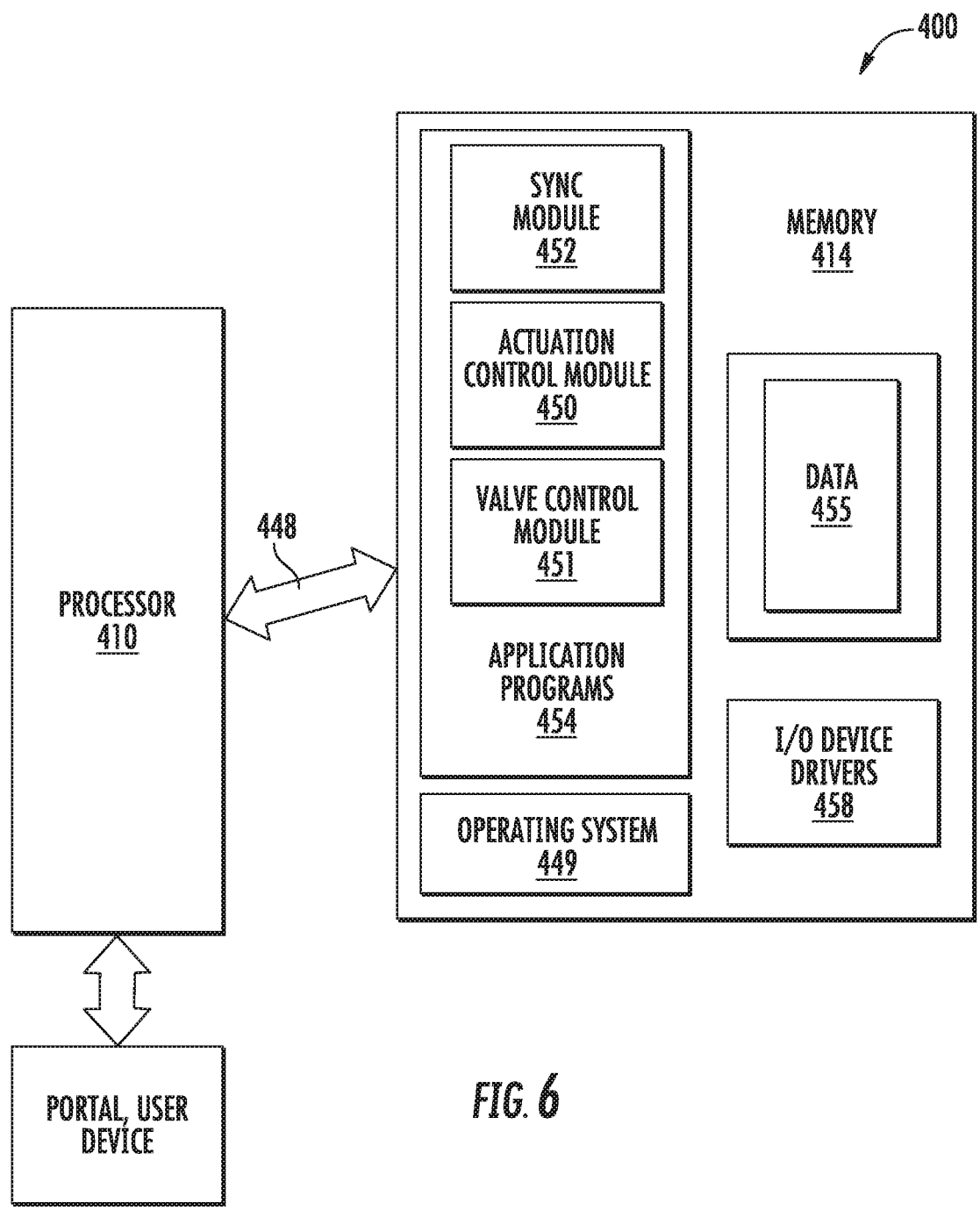
FIG. 6 is a block diagram of a data processing system according to some embodiments.

FIG. 6 illustrates a data processing system 400 with a processor 410 and tangible memory 414 that may be used to carry out at least some of the operations described herein. The controller 50 (FIGS. 1, 2) may be in communication with and/or comprise the processor 410 and/or the memory 414. The processor 410 can communicate with the memory 414 via an address/data bus 448. The processor 410 may be, for example, a commercially available or custom microprocessor. The memory 414 is representative of the one or more memory devices containing software and data used to perform operations in accordance with some embodiments of the present invention. The memory 414 may include, but is not limited to, the following types of devices: cache, ROM, PROM, EPROM, EEPROM, flash, SRAM, and DRAM.

As shown in FIG. 6, the memory 414 may contain an operating system 449; the operating system 449 may manage the dispensing system 10 software and/or hardware resources and may coordinate execution of programs by the processor 410. The system 400 can include a Valve control Module 451, an Actuation Control Module 450 and a Synch Module 452 so that the actuation of the canister(s) occurs after the valve is open and when air flow is in an inhalation direction (toward a patient).

Figure 7:
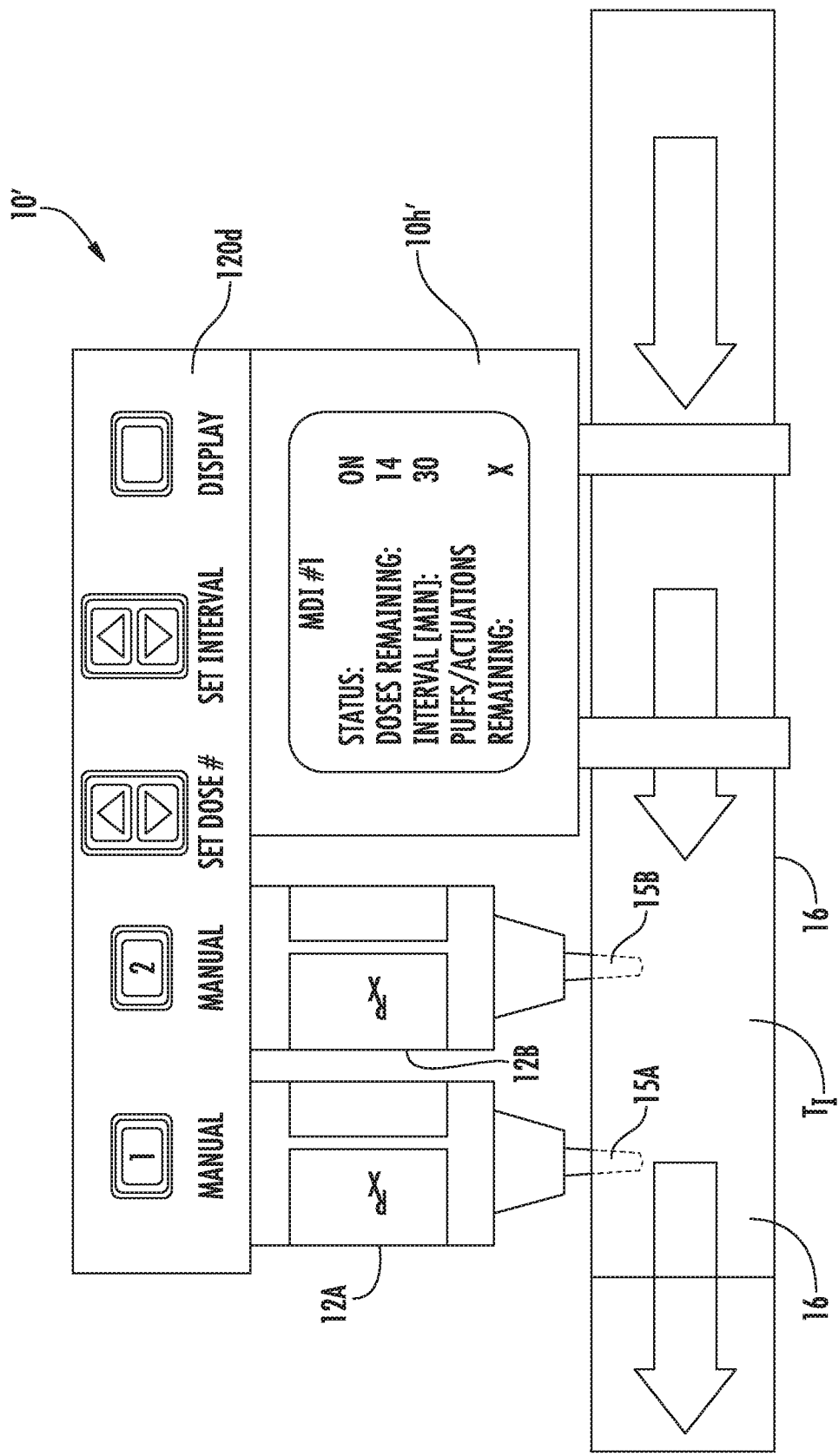
FIG. 7 is a schematic of another example of an automated drug dispensing system according to embodiments of the present invention.

Another embodiment of an automated control and dispensing system 10' is illustrated in FIG. 7. The system 10' can include any or all the components and features described above with regard to the system 10 shown in FIGS. 1 and 2, for example. The system 10' can be configured to automate the delivery of medication from a plurality of (shown as two) canisters 12A, 12B. It is contemplated that a unit similar to the unit 10' may accommodate more than two MDIs. For example, the additional MDIs may be aligned with the MDIs 12A, 12B shown in FIG. 2. Alternatively, a second housing may extend away from the tubular connector 16 to accommodate additional MDI canisters 12. For example, a second housing may be circumferentially and/or axially spaced apart from the unit 10'. By way of further example, the housing 10h' could be rotated by 90 degrees on the vertical axis, and multiple devices could be attached onto a longer connector 16 that has a row of multiple entry ports.

The dispensing systems 10, 10' may include a memory, such as the memory 412 (FIG. 6) or other memory, to allow data acquisition capability. In particular, the memory may provide for data capture such that data can be downloaded.

The dispensing system 10, 10' can include a USB interface, an Ethernet interface, wireless transmission capabilities, Bluetooth or other connectivity to transmit data to one or more defined devices 120 (FIG. 2). The data may then be used for patient records, for assessing the performance of the unit, and for other purposes as would be understood by those of skill in the art.

In the embodiments described above, medication from an MDI such as the MDI canister 12 is typically injected into the ventilator flow circuit 60c via the interior of the connector 16. In some other embodiments, the connector may take a different form.

In some embodiments, the dispensing system 10 may be designed with the option to allow the patient the ability to self-administer an unscheduled "puff" or dose of medication with a manual override control that may be attached to or integrated into a hospital bed or may be a device placed within reach of the patient P, such as a control with a depressible button or the like. The control may allow the patient P to self-administer an unscheduled "puff" or dose of medication whenever the patient P senses the need and without having to call a caregiver. This may be useful because mechanical ventilator patients generally cannot easily communicate their needs. For example, this feature may be useful for critical but non-sedated patients.

The system 10, 10' may include safety control of patient-initiated drug dispensation within safe parameters as determined by a physician and/or programmed by the unit operator.

The dispensing system 10, 10' may provide a diagnostic platform and may be used with patients in vivo. The systems 10, 10' can provide for the administration of inhaled particles, whether they be small chemical agents, small peptide/proteins, whole organisms such as a virus vector, or a radioactive labeled particles (e.g., nucleotide/carbohydrate/gas) that can be thought of as a "drug or pharmaceutical agent." This agent may be used for a clinical effect to measure, diagnose, and/or treat any physiologic process or condition by measuring the exhaled gas to make a physiological reading or measurement to determine a specific state or condition. The device 10, 10' may then use the measured specific state based on the pre-determined/programmed protocol to automatically initiate specified care/treatment (e.g., inhaled antibiotics/inhaled steroids/radioactive gold particles or initiate ventilator weaning) in an automated fashion based on the disease state/condition and/or the physiologic parameter that is chosen to be measured. In various embodiments, the device 10, 10' may be used for only administration purposes, for only detection purposes, and for both administration and detection purposes. In some embodiments, the detected condition or state may be displayed for a clinician or physician; for example, the detected condition or state may be displayed on a display 120d.

Techniques used to diagnose/measure in the device include but are not limited to gas chromatography/capillary GC, liquid chromatography (HPLC/UHPLC), multidimensional chromatography, DNA/RNA sequencing, biophotonic sensors/photometry, biospectroscopy, single cell/multicell flow cytometry, optical microscopy, optical analysis with remote and automated/televised monitoring, mass spectroscopy, IR spectroscopy, antibody labeled ELIZA, gas volitile and non-volitile analysis, small molecule/protein, peptide, carbohydrate hydrocarbon analysis, chemical vapor deposition, calimetry, bioluminensence/luminensence, ion exchange, or any other analytical bio/radio/histochemistry technique that could be used to measure exhaled breath condensate.

The dispensing systems 10, 10' can include an optional exhaled gas sensor 135 (FIG. 2). After the patient has inhaled the particles and then exhaled, exhaled gas flow may be measured using the exhaled gas measurement sensor 135. The exhaled gas measurement sensor 135 can measure exhaled breath condensate using one or more of the techniques described above. For example, the amount or concentration of exhaled "waste gas" could be measured after the particles have been administered.

A physiological reading or measurement (or exhaled gas measurement EGM) can be communicated from the sensor 135 to the controller 50. The controller or outside device can determine a specific state or condition of the patient based on the EGM. The controller may then adjust a medication dosing or timing based on the specific state or condition of the patient. The device 10 may include a display 120d which may display parameters related to the determined specific state or condition of the patient and/or the current medication dosing or frequency and/or any adjustment thereto.

The foregoing is illustrative of the present invention, and is not to be construed as limiting thereof. Although exemplary embodiments of this invention have been described, those skilled in the art will readily appreciate that many modifications are possible in the exemplary embodiments without materially departing from the novel teachings and advantages of this invention. As such, all such modifications are intended to be included within the scope of this invention. The scope of the invention is to be defined by the following claims.

That which is claimed is:

1. A dispensing system for a ventilator circuit, comprising:
   a ventilator flow circuit comprising an inhalation flow path comprising a normal inhalation flow path segment with a heat and moisture exchanger (HME), wherein the ventilator flow circuit comprises a Y connector with a leg that couples to and is in line with the HME and with a first branch that resides upstream of the HME and the leg and that defines part of the normal inhalation flow path segment and a second branch that resides downstream of the HME and adjacent to the first branch and defines part of an exhalation flow path;
   a flow sensor in communication with the ventilator flow circuit;
   an automated dispensing system with an actuator and a pressurized canister residing upstream of the Y connector;
   a bypass inhalation flow path comprising a bypass inhalation flow path segment that resides downstream of the pressurized canister;
   at least one electromechanical valve residing in the inhalation flow path, upstream of the Y connector and configured to selectively operate to define either (i) a closed bypass inhalation flow path and an open normal inhalation flow path segment with the HME or (ii) an open bypass inhalation flow path and a closed normal inhalation flow path segment with the HME, wherein the at least one electromechanical valve resides downstream of the actuator and the pressurized canister; and
   at least one controller in communication with the flow sensor, the actuator and the at least one electromechanical valve, wherein the at least one controller directs the at least one electromechanical valve to open the bypass inhalation flow path and close the normal inhalation flow path segment through the HME only when the flow sensor indicates air flow is in an inhalation direction, and wherein, once the bypass inhalation flow path is open, the at least one controller directs the at least one actuator to dispense medication in the air flow path so that the medication travels through the bypass inhalation flow path to a patient.

2. The system of claim 1, wherein after the actuator actuates, the at least one controller then directs the at least one electromechanical valve to close the bypass path and open the normal inhalation flow path segment with the HME after medication delivery is complete.

3. The system of claim 1, wherein the system is configured to automatically dispense medication from the pressurized canister based on the patient's current physiologic status including, but not limited to, one or more measurements of one or more of the following parameters: heart rate, respiratory rate, airway resistance, blood pressure, minute ventilation, end tidal carbon dioxide measurements, temperature, EEG monitoring, cardiac telemetry rhythm/ECG monitoring, oxygen saturation/oximetry monitoring peripheral or central, nitric oxide exhaled, and wherein the one or more parameters are electronically periodically or continuously directly or indirectly electronically monitored and analyzed by at least one processor in communication with the dispensing system.

4. The system of claim 3, wherein a dose and/or dispensing delivery time are electronically adjustable by the automated dispensing system, and wherein the bypass flow path extends upstream of the Y connector to a unit housing providing at least part of the ventilator flow circuit.

5. The system of claim 4, wherein the dose and/or dispensing delivery time are adjusted automatically based on a detected change in physiologic status based on the one or more parameters being electronically monitored.

6. The system of claim 4, wherein the at least one controller is in communication with a computer network.

7. The system of claim 3, wherein the at least one controller is in communication with a smartphone, electronic notebook or other portable computing device providing a user interface.

8. The system of claim 1, wherein the system is configured to electronically transmit data over a computer network to one or more defined devices to thereby provide patient data records and/or provide performance evaluation records of respective ventilator systems.

9. The system of claim 1, wherein the system comprises an electronic reader that is configured to identify a medication associated with the pressurized canister, wherein the system is configured to review patient data records including prescribed medications and any drug allergies and electronically alert an operator if a drug incompatibility is identified.

10. The system of claim 1, wherein the system is configured to transmit data over a computer network and remotely electronically evaluate patient data records and/or performance of the system.

11. The system of claim 1, wherein the system is configured to electronically evaluate exhaled gas of a respective patient, electronically identify a physiologic state or condition and adjust a medication dose or timing based on the electronically evaluated exhaled gas.

12. A dispensing system for a ventilator circuit, comprising:
- a ventilator flow circuit comprising a normal inhalation flow path with a heat and moisture exchanger (HME);
- a flow sensor in communication with the ventilator flow circuit;
- an automated dispensing system with an actuator and a pressurized canister residing upstream of the HME;
- a bypass inhalation flow path residing downstream of the pressurized canister;
- at least one electromechanical valve residing in the inhalation flow path to selectively open a valve which is normally closed to define a closed bypass inhalation flow path; and
- at least one controller in communication with the flow sensor, the actuator and the at least one electromechanical valve, wherein the at least one controller opens the at least one electromechanical valve to open the bypass inhalation flow path and close the normal inhalation flow path through the HME only when the flow sensor indicates air flow is in an inhalation direction, and wherein, once the at least one electromechanical valve is open, the at least one controller directs the at least one actuator to dispense medication in the air flow path so that the medication travels through the bypass inhalation flow path to a patient,
wherein the ventilation flow circuit is connected to a ventilator machine of a ventilator unit, wherein the ventilation flow circuit comprises tubing with an exhalation flow path and comprises at least one Y connector held by a housing of the ventilator unit and comprises a first leg that connects to the normal inhalation flow path with the HME and comprises a second leg that connects to the bypass inhalation flow path, wherein the bypass inhalation flow path is devoid of an HME,
wherein the flow sensor provides patient breathing flow direction data to the at least one controller,
wherein the at least one Y connector includes a first Y connector at least partially held in the housing of the ventilator unit, a second Y connector downstream of the HME that merges the normal inhalation flow path with the bypass inhalation flow path configured to be proximate a patient in use, and a third Y connector coupled to the HME on a side opposing the second Y connector, and wherein the third Y connector has a first leg coupled to the normal inhalation flow path and a second leg coupled to the exhalation flow path.

* * * * *